(12) United States Patent
Grayden et al.

(10) Patent No.: US 7,010,354 B1
(45) Date of Patent: Mar. 7, 2006

(54) SOUND PROCESSOR FOR COCHLEAR IMPLANTS

(75) Inventors: David Bruce Grayden, Heathmont (AU); Graeme Milbourne Clark, Eltham (AU)

(73) Assignee: The Bionic Ear Institute, East Melbourne (AU)

( * ) Notice: Subject to any disclaimer, the term of this patent is extended or adjusted under 35 U.S.C. 154(b) by 600 days.

(21) Appl. No.: 10/069,846

(22) PCT Filed: Sep. 1, 2000

(86) PCT No.: PCT/AU00/01038

§ 371 (c)(1),
(2), (4) Date: May 30, 2002

(87) PCT Pub. No.: WO01/19135

PCT Pub. Date: Mar. 15, 2001

(30) Foreign Application Priority Data

Sep. 2, 1999 (AU) .................................... PQ2612

(51) Int. Cl.
*A61N 1/36* (2006.01)
(52) U.S. Cl. ...................................... 607/57
(58) Field of Classification Search ............ 607/55–57, 607/66, 70, 137
See application file for complete search history.

(56) References Cited

U.S. PATENT DOCUMENTS

| 4,063,048 | A | 12/1977 | Kissiah, Jr. |
| 4,284,856 | A | 8/1981 | Hochmair et al. |
| 5,095,904 | A * | 3/1992 | Seligman et al. ............. 607/57 |
| 5,271,397 | A | 12/1993 | Seligman et al. |
| 5,597,380 | A | 1/1997 | McDermott et al. |
| 5,601,617 | A | 2/1997 | Loeb et al. |
| 5,749,912 | A | 5/1998 | Zhang et al. |
| 5,800,475 | A | 9/1998 | Jules |
| 5,922,016 | A | 7/1999 | Wagner |

FOREIGN PATENT DOCUMENTS

WO WO 91/03903 3/1991

OTHER PUBLICATIONS

Loizou, "Introduction to cochlear implants," Sep. 1998, IEEE Signal Processing Magazine, pp. 101-130.*

(Continued)

*Primary Examiner*—Kennedy Schaetzle
(74) *Attorney, Agent, or Firm*—Scully, Scott, Murphy & Presser

(57) ABSTRACT

An improved sound processor for a cochlear implant having electrodes for stimulating the auditory nerve, including means for receiving sounds, means for processing the sounds and converting them to electrical stimulation signals for application to the electrodes of the cochlear implant for stimulation of the auditory nerve, said sound processing means including means for generating electrical signals to be applied to the basal electrodes having different predetermined rates of stimulation and the implant having basal electrodes and apical electrodes and the means for generating electrical signals to be applied to the apical electrodes have a different rate of stimulation, the electrical signals to be applied to the basal electrodes having a higher rate of stimulation than the electrical signals to be applied to the apical electrodes.

12 Claims, 1 Drawing Sheet

OTHER PUBLICATIONS

A Multipeak Feature Extraction Coding Strategy for a Multi Channel Cochlear Implant, Dawn Burton Koch, PhD, et. al, 03/01/920, No. 3, pp. 28-29 and 32.

"Melody Recognition and Musical Interval Perception by Deaf Subjects Stimulated With Electrical Pulse Trains Through Single Cochlear Implant Electrodes", Journal of the Acoustical Society of America vol. 98, No. 2 pt 1 issued Aug. 1995, pp. 886-895.

"Electrode Ranking of "Place Pitch" and Speech Recognition in Electrical Hearing", Journal of the Acoustical Society of America, vol. 98, No. 4 issued 1995, pp. 1987-1999.

* cited by examiner

SOUND PROCESSOR FOR COCHLEAR IMPLANTS

FIELD OF THE INVENTION

This invention relates to improvements in sound processors for cochlear implants, and more particularly to a Differential Rate Sound Processor (DRSP).

BACKGROUND OF THE INVENTION

The multi-channel cochlear implant was first implanted in 1978. Early signal processing designs extracted the second formant (F2) and pitch (F0) to control electrode stimulation. The frequency of F2 controlled the location of electrode stimulation, and F0 controlled the rate of stimulation. This was later improved by also extracting the first formant (F1) and adding a second stimulated electrode for each pitch period. The MULTI-PEAK (MPEAK) stimulation strategy added stimulation of a number of fixed electrodes to better represent high-frequency information. The next stages of development were the SMSP and SPEAK strategies. These were a departure from the others at they used a fixed stimulation rate and stimulated electrodes that corresponded to maxima in the sound spectra. Another fixed-rate strategy, CIS, was developed overseas. This strategy stimulated all of a small number of electrodes to represent the sound spectra. All of the above processing strategies involve fixed-rate sound processing.

The named inventors have determined that some speech features are better perceived using low-rates of simulation, while some are better perceived using high rates of stimulation. Higher rates of stimulation present more information about phonetic manner of articulation, but spectral information tends to be smeared at such higher rates.

SUMMARY OF THE INVENTION AND OBJECT

It is an object of the present invention to provide an improved sound processor for use with cochlear implants in which the problems associated with fixed rate stimulation are ameliorated.

The invention provides in one form an improved sound processor for a cochlear implant having electrodes for stimulating the auditory nerve, including means for receiving sounds, means for processing the sounds and converting them to electrical stimulation signals for application to the electrodes of the cochlear implant for stimulation of the auditory nerve, said sound processing means including means for generating electrical signals to be applied to the electrodes having different predetermined rates of stimulation.

In this first form of the invention, the cochlear implant preferably has basal electrodes and apical electrodes and the means for generating electrical signals to be applied to the apical electrodes have a different rate of stimulation, the electrical signals to be applied to the basal electrodes having a higher rate of stimulation than the electrical signals to be applied to the apical electrodes.

By causing stimulation of the basal electrodes at a higher rate of stimulation than the apical electrodes, the manner of articulation features of speech will be more optimally presented to the cochlear implant user, leading to improved speech understanding performance. High rates of stimulation at the basal electrodes will present good information about temporal events and frication. The low rates of stimulation of the apical electrodes will present good spectral information in this regard, where most place of articulation features reside.

In a preferred embodiment, the more apical electrodes will be chosen as those that contain the voice bar and lower formants of speech. In this frequency region, spectral detail is important and the apical electrodes will be stimulating using a stimulation rate of between about 250 cycles per second and about 800 cycles per second, depending on the user. By adopting stimulation rates falling within the above range, better information about place of articulation of speech, which is largely represented by the formant structure, is obtained by the user.

The more basal electrodes represent higher frequency components of the incoming sound, and higher rates of stimulation of these electrodes will be used to better represent noise and more precisely present information about temporal events such as rapid changes in amplitude. The latter is important for perception of manner of articulation and voicing. These electrodes will be stimulated at a higher rate than the apical electrodes, with stimulation rates at or above about 800 cycles per second, and preferably up to about 1600 cycles per second, being selected depending on the user.

In the case of an implant having 20 electrodes available for stimulation, the apical electrodes are electrodes 0 to 12, and the basal electrodes are electrodes 13 to 19. The apical electrodes represent sound frequencies from 0 to about 2700 Hz, while the basal electrodes represent frequencies from about 2700 Hz to about 7900 Hz. The stated apical electrode frequencies are sufficient to contain the first three formants of most speech.

In a particularly preferred form of the invention, the apical electrodes are stimulated at about 250 cycles per second while the basal electrodes are stimulated at about 1500 cycles per second. To ensure that stimulation levels are suitable for these different rates, the threshold (T) levels and comfort (C) levels of the patient are carefully set. The electrodes to be stimulated are chosen by selecting the eight largest spectral energies within filterbanks derived from the Fast Fourier Transform (FFT) or the Discrete Wavelet Transform (DWT) which is performed by the processor.

In another form, the invention provides an improved sound processor for a cochlear implant having electrodes for stimulating the auditory nerve, including means for receiving sounds, means for processing the sounds and converting to electrical stimulation signals for application to the electrodes of the cochlear implant whereby the auditory nerve is electrically stimulated, said sound processing means having means for varying the rate of stimulation of the electrical stimulation signals depending on the parameters of the sound received by the sound receiving means.

By varying the rate of stimulation of the cochlear implant electrodes depending on the incoming speech signal, key speech features will be more optimally presented to the cochlear implant user thereby leading to improved speech understanding performance.

In a preferred form of this aspect of the invention, the sound processing means will be programmed to continually adjust the rate of stimulation of the electrical stimulation signals depending on the parameters of the incoming speech signal. To this end, the incoming speech signal will be processed to detect events that are better represented using a higher rate of stimulation. Such events include plosive onset bursts, frication and other rapid spectral changes. The rate of stimulation across all electrodes will be increased for the average duration of these events. The standard rate will be between 250 cycles/s and 800 cycles/s depending on the user. The higher rate will be above about 800 cycles/s, and preferably up to about 1600 cycles/s, also depending on the user.

BRIEF DESCRIPTION OF THE DRAWINGS

In order that the invention may be more readily understood, one presently preferred embodiment of the invention will now be described; with reference to the accompanying drawings in which.

DESCRIPTION OF PREFERRED EMBODIMENT

Figure 1:
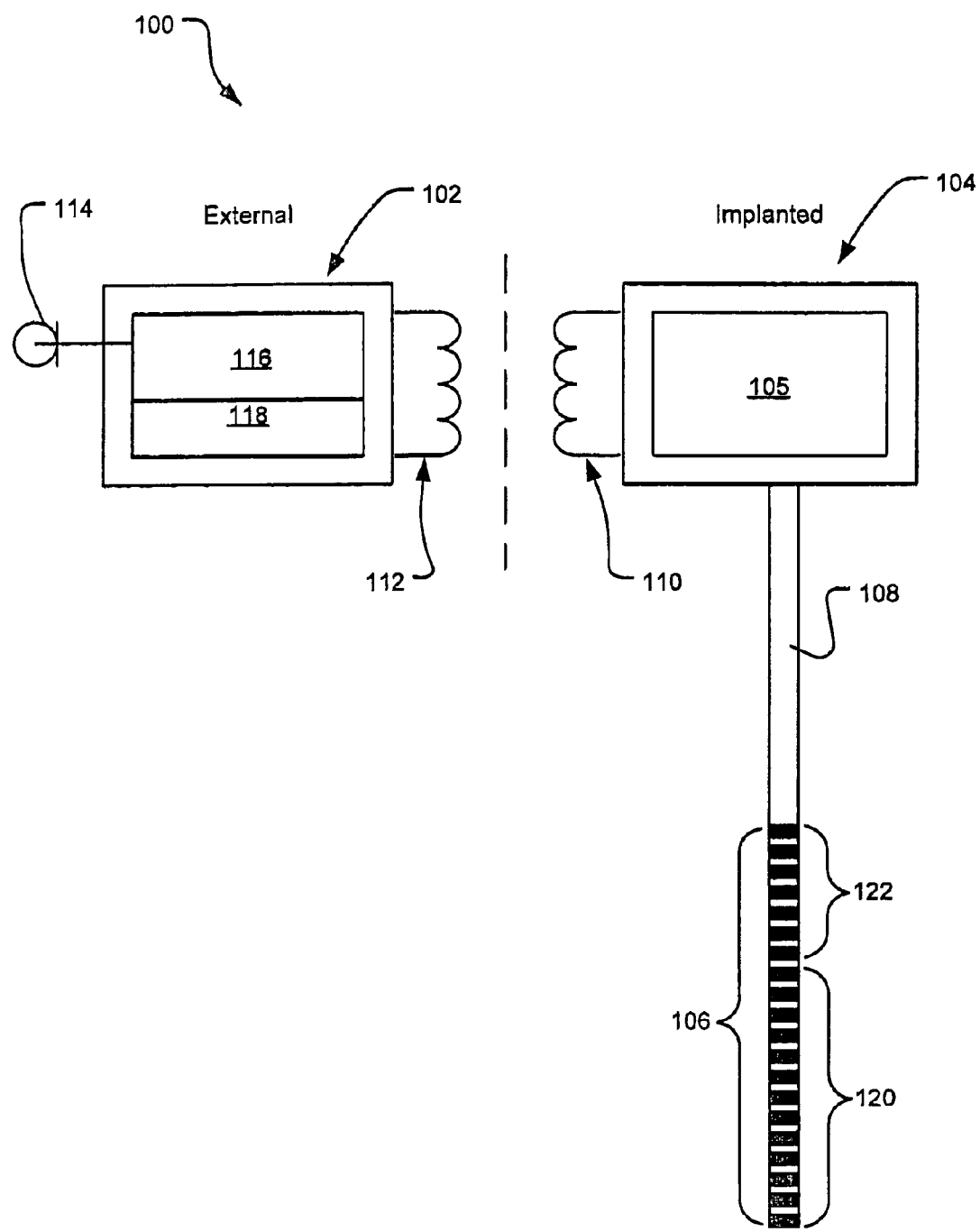
FIG. 1 is a block diagram, of a cochlear implant including a sound processor in accordance with an embodiment of the present invention.

FIG. 1 depicts a cochlear implant system 100 embodying the present invention. In general, the cochlear implant system 100 comprises an external sound processor unit 102 and an implanted receiver-stimulator unit (RSU) 104. The RSU 104 includes an electrode array 106 is implanted into the cochlea. In the embodiment of the invention described the electrode array 106 comprises a number of rings or bands of platinum molded with a flexible silastic carrier. The electrode wires pass in a cable 108 from the electrode to the RSU 104 via a connector. The RSU 104 receives information and power from the externally worn sound processor unit 102 through a tuned receiving coil 110 attached to the RSU 104 and mounted just beneath the skin. The RSU 104 includes means 105 for generating electrical stimulating pulses to the electrode array 106. The power and data on which electrode to stimulate, and with what intensity is transmitted across the skin to the RSU 104 from the sound processor unit 102 using an inductive link 112 operating at radio frequencies. In normal operation, the sound processor 108 picks up acoustic stimuli from a microphone 114 conveniently worn, and extracts from the signal information which is used to determine stimulation electrode rate and amplitude.

Because each patient's response to electrical stimulation is different, it is necessary to configure each patient's sound processor 102 to his or her own requirements. Thus the sound processor includes signal processing means 116 for applying a sound processing strategy, as described below. The sound processor unit 102 also has an Erasable Programmable Read Only Memory EPROM 118 which includes data and instructions to control the operation of the signal processing means 116 and which is programmed with parameters to suit each patient.

The invention is preferably designed for use with the CI-24M Cochlear Implant as manufactured by Cochlear Ltd, and as described in U.S. Pat. No. 4,532,930, the contents of which are incorporated herein by cross-reference, and later patents by Cochlear Ltd to be found in the patent literature.

Although the CI-24M Implant will be used in most cases, the invention could be applied to any implant that uses pulsatile stimulation. The stimulation strategy is based on the Spectral Maxima Sound Processor (SMSP), which is described in U.S. Pat. No. 5,597,380 and Australian Patent 657959, the contents of which are incorporated herein by cross reference although other strategies may be used with similar results. For example, the SPEAK strategy as discussed in U.S. Pat. No. 5,597,380, the contents of which are incorporated by cross reference.

The electrode selection strategy from the SMSP is varied to ensure that electrodes are stimulated at the desired predetermined frequencies for each cycle of stimulation. The preferred signal processing device will be the SPEAR processor, which is currently under development at The Bionic Ear Institute, and which is described in the following paper:

Zakis, J. A. and McDermott, H. J. (1999). "A new digital sound processor for hearing research," Proceedings of the Inaugural Conference of the Victorian Conference of the Victorian Chapter of the IEEE Engineering in Medicine and Biology Society, February 22–23, pp. 54–57. The contents of this paper are similarly incorporated herein by cross reference.

The processor is a generic processor based on the Motorola DSP56300 family, such as the DSP56302, or the DSP56309, although any digital signal processor, including those produced by Cochlear Ltd and their competitors, could be used to run the differential rate sound processor program of the present invention, provided they have adequate processing speed.

In the implementation of the first form of the invention, the differential rate stimulation processor software embodying the invention is downloaded to the SPEAR processor 116, and stored on EPROM 118. Patient map details, including frequency bands, threshold (T) levels and comfort (C) levels, are also stored on the device, Monopolar stimulation mode is used to reduce current levels and for longer battery life.

For the case where 20 electrodes 106 are available for stimulation, the apical electrodes 126 are electrodes 0 to 12, and the basal electrodes 122 are electrodes 13 to 19. The apical electrodes 120 then represent frequencies from 0 to 2700 Hz; the basal electrodes 122 represent frequencies from 2700 Hz to 7900 Hz. The stated apical electrode frequencies are sufficient to contain the first three formants of most speakers' speech.

The apical electrodes 120 are stimulated at about 250 cycles/s and the basal electrodes 122 at about 1500 cycles/s. The patient's T and C levels are carefully set to ensure that stimulation levels are suitable for the two different rates and adjustments made if necessary. The electrodes 102 to be stimulated are chosen by selecting the eight largest spectral energies within filter banks derived from the Past Fourier Transform (FFT) or the Discrete Wavelet Transform (DWT).

The values quoted above are examples. Patient-to-patient variability is large and some need higher stimulation rates on the apical electrodes and/or lower stimulation rates on the basal electrodes 122. These are determined for each individual by evaluating a number of rate combinations in every day usage.

By using the Differential Rate Sound Processor (DRSP) program of the invention, features of speech will be more optimally presented to the cochlear implant user leading to improved speech understanding performance.

In the implementation of the second aspect of the invention, the software necessary to provide a variable rate of stimulation depending on the incoming speech signal is downloaded to the SPEAR processor 116 and stored on an EPROM 118. Patient map details, including frequency bands, threshold (T) levels and comfort (C) levels, are also stored on the device. Monopolar stimulation mode is used to reduce current levels and for longer battery life.

The standard rate of stimulation is about 250 cycles/s and the higher rate is about 1500 cycles/s. The patient's T and C levels are carefully set to ensure that stimulation levels are suitable for the two different rates. The electrodes to be stimulated are chosen by selecting the eight largest spectral energies within filterbanks derived from the Fast Fourier Transform (FFT) or the Discrete Wavelet Transform (DWT).

The changes in spectral energies and the amount of frequency energy are monitored over time. When there is a significantly large change between frames separated by the period of the lower stimulation rate then the higher stimulation rate is used for 50 ms. This procedure locates plosive bursts and other rapid spectral changes. The higher stimulation rate is also used when the ratio of energy below about 300 Hz to that above about 2000 Hz is less than about 0.5. This locates phonemes with significant frication.

The values quoted above are examples. Patient-to-patient variability is large and some need a higher stimulation rate for the standard rate and/or a lower stimulation rate for the higher rate. These are determined for each individual by evaluating a number of rate combinations in every day usage. Thresholds for changes in energy and ratio of energies are also adjustable for each individual.

What is claimed is:

1. A sound processor for a cochlear implant having electrodes for simulating the auditory nerve, including means for receiving sounds, means for processing the sounds and converting them to electrical stimulation signals for application to the electrodes of the cochlear implant for stimulation of the auditory nerve, wherein the cochlear implant has basal electrodes and said sound processing means including means for generating electrical signals to be applied to the basal electrodes having different predetermined rates of stimulation and the cochlear implant has apical electrodes and the means for generating electrical signals to be applied to the apical electrodes have a different rate of stimulation, the electrical signals to be applied to the basal electrodes having a higher rate of stimulation than the electrical signals to be applied to the apical electrodes.

2. The sound processor of claim 1, wherein the more apical electrodes are selected for stimulator signals that represents the voice bar and lower formants of the sounds.

3. The sound processor of claim 2, where the more apical electrodes apply stimulation signals having a stimulation rate of between about 250 cycles per second and about 800 cycles per second depending on the user, to provide precise spectral and place of articulation information.

4. The sound processor of claim 1, wherein the more basal electrodes apply stimulation signals having a stimulation rate of at or above about 800 cycles per second depending on the user, to provide precise information about temporal events and frication.

5. The sound processor of claim 1, wherein the sound processor includes, a twenty (20) electrode implant, the apical electrodes are electrodes 0 to 12 and the basal electrodes are electrodes 13 to 19, the apical electrodes representing sound frequencies from 0 to about 2700 Hz, while the basal electrodes represent frequencies from about 2700 Hz to about 7900 Hz, the apical electrode frequencies, are sufficient to contain the first three formants of most speakers speech.

6. The sound processor of claim 1, wherein the apical electrodes are stimulated at about 250 cycles per second and basal electrodes are stimulated at about 1500 cycles per second.

7. The sound processor of claim 6, wherein, the electrodes to be stimulated are chosen by selecting eight largest spectral energies within filter banks derived from a Fast Fourier Transform (FFT) or a Discrete Wavelet Transform (DWT) which is performed by the processor.

8. A sound processor as claimed in claim 1, wherein said sound processing means include means for varying the rate of stimulation of the electrical stimulation signals depending on the-parameters of sound received by the sound receiving means.

9. The sound processor of claim 8, wherein the sound processing means is programmed to continually adjust the rate of stimulation of the electrical stimulation signals depending on the parameters of the received sound signal.

10. The sound processor of claim 8, wherein the received sound signal is processed to detect events that are better presented using a higher rate of stimulation.

11. The sound processor of claim 1, wherein the implant is one which uses pulsatile stimulation.

12. The sound processor of claim 1, wherein the means for processing the sounds include a SPEAR processing device programmed using a Differential Rate Sound Processor (DRSP) program to optimally present the features of speech to the implant.

* * * * *